United States Patent [19]
Fox et al.

[11] Patent Number: 5,186,965
[45] Date of Patent: Feb. 16, 1993

[54] CALCIUM CITRATE MALATE COMPOSITION

[75] Inventors: Mary M. Fox, Fairfield; David C. Heckert, Oxford, both of Ohio; Kenneth R. Luhrsen, Aurora, Ind.

[73] Assignee: The Procter & Gamble Company, Cincinnati, Ohio

[21] Appl. No.: 808,116

[22] Filed: Dec. 16, 1991

Related U.S. Application Data

[63] Continuation of Ser. No. 608,055, Oct. 31, 1990, abandoned, which is a continuation-in-part of Ser. No. 537,313, Jun. 14, 1990, abandoned.

[51] Int. Cl.$^5$ .............................................. A23L 1/304
[52] U.S. Cl. ...................................... 426/74; 562/582; 562/584; 424/600
[58] Field of Search .................. 426/74; 562/582, 584; 424/49, 600

[56] References Cited

U.S. PATENT DOCUMENTS

| | | | |
|---|---|---|---|
| 4,551,342 | 11/1985 | Nakel et al. | 426/548 |
| 4,722,847 | 2/1988 | Heckert | 426/74 |
| 4,737,375 | 4/1988 | Nakel et al. | 426/590 |
| 4,786,510 | 7/1988 | Nakel | 426/74 |
| 4,786,518 | 11/1988 | Nakel | 426/531 |
| 4,830,862 | 5/1989 | Braun et al. | 426/74 |
| 4,992,282 | 2/1991 | Mehansho | 426/72 |
| 4,994,283 | 2/1991 | Mehansho | 426/74 |

FOREIGN PATENT DOCUMENTS 56-097248  9/1981  Japan .

OTHER PUBLICATIONS

Copley 1963 Food Dehydration vol. I pp. 156–165 Westport Conn. The AVI Publishing Co., Inc.
Smith, et al., Calcif. Tissue Int. (1987) 41:351-352.
Miller, et al., Am. J. Clin. Nutr. (1988), 48:1291-1294.
Miller, et al., Clinica Chimica Acta, (1989) 183:107-114.
Kochanowski, B. A., J. Nutr. (1990) 120: 876-881.

*Primary Examiner*—Carolyn Paden
*Attorney, Agent, or Firm*—Rose Ann Dabek; K. L. Stewart; Jerry J. Yetter

[57] ABSTRACT

A metastable complex of calcium, citrate and malate is disclosed. This material is highly bioavailable, and is soluble in both neutral and acid solutions. The salt is prepared by the reaction of calcium carbonate, calcium hydroxide or calcium oxide with citric and malic acids in aqueous solution. The reaction mixture is dried at a temperature of less than 100° C., and the resultant solid is a metastable solid. The solid can be ground to reduce the particle size for easier tabletting or adding to foods and beverages. Preferred salts are neutral and acidic salts which can be expressed by molar ratios.

18 Claims, No Drawings

CALCIUM CITRATE MALATE COMPOSITION

This is a continuation of application Ser. No. 07/608,055, filed on Oct. 31, 1990.

Which is a continuation-in-part of application Ser. No. 07/537,313 filed Jun. 14, 1990, now abandoned.

TECHNICAL FIELD

This invention relates to a soluble calcium source comprising specific molar ratios of calcium, citrate and malate. The composition is more soluble than calcium citrate or calcium malate alone, and when prepared by the process herein, consists of a metastable complex salt which is distinct from either pure calcium citrate or pure calcium malate.

BACKGROUND OF THE INVENTION

Calcium is a mineral that is important for building bones and teeth. One of the problems with supplementation of the diet with calcium is that all sources of calcium are not equally soluble or bioavailable. In addition, some calcium sources are not as pure as other sources. For example, calcium carbonate derived from bone meal, oyster shell, or other biological origins contains trace amounts of lead and other minerals. Some calcium carbonates also contain silica. Therefore, it is necessary to take additional amounts of these materials to achieve the same calcium level as those taken from synthetic sources which are essentially pure calcium carbonate.

Calcium citrate is poorly soluble in water; 1 gram of calcium citrate dissolves per 1050 grams of cold water. Calcium malate exhibits a similar solubility. Calcium hydroxide is only slightly soluble in water, and it absorbs carbon dioxide from the air readily forming calcium carbonate.

In addition, calcium salts readily hydrate even when stored in dry cool places. Therefore, the amount of calcium being delivered may be even less than expected because of the large amount of water absorbed by the salts.

Therefore a calcium salt which is readily bioavailable and which is readily soluble in neutral solutions as well as acidic solutions is highly desirable. This would allow the calcium salt to be added to neutral as well as acid foods in a soluble form and to be an effective supplement. Granular salts can produce a gritty taste in foods and beverages if they are not soluble or are too large in particle size.

It is therefore an object of this invention to produce a calcium salt which is highly bioavailable and which is readily soluble in water.

BACKGROUND ART

Japanese patent application Sho 56/097,248 (Tanaka, 1981) discloses a calcium citrate malate salt of increased solubility. This salt is a 5:2:2 ratio of calcium:citrate:malate. The applicant suggests that 2 molecules of calcium malate are associated with 1 molecule of calcium citrate. The product is described as a white crystalline powder which is soluble at 0.5 g/100 ml of water at 20° C. and which has a pH of 6 to 6.5. The product is formed by mixing calcium carbonate with citric and malic acids in water at 50° C. to 60° C. and separating the white crystalline material from the mother liquor. When the product is dry (oven drying is used) the temperature is raised to 110° C.–120° C. to sterilize the powder. Alternatively a product is made using calcium chloride, sodium citrate and sodium malate.

Calcium citrate malate has been made in beverages. U.S. Pat. No. 4,737,375 issued to Nakel et al describes beverages nutritionally supplemented with calcium to which citric and malic acids are added.

U.S. Pat. No. 4,722,847 issued to Heckert (1988) describes calcium citrate malate in beverages and the preparation of the material in a beverage format.

European Patent to Jacobs entitled "Novel Calcium Supplements", 304,987 (1989), discloses calcium citrate malate materials that have a 6:2:3 molar ratio.

SUMMARY OF THE INVENTION

A process for forming a soluble, metastable calcium citrate malate material comprising:
  a) mixing a calcium source selected from the group consisting of calcium carbonate, calcium oxide or calcium hydroxide with citric and malic acids in water until the calcium is neutralized;
  b) drying the total mixture at less than 90° C.; and optionally,
  c) grinding the solid to a particle size of less than 1 millimeter.

The drying can be done by freeze drying, spray drying oven drying, convection or forced air drying. The calcium:citrate:malate ratio can vary.

DETAILED DESCRIPTION OF THE INVENTION

As used herein the term, "calcium citrate malate" refers to a mixture of calcium, citrate and malate. The specific ratios will be defined as the ratio of calcium to citrate to malate. All ratios of calcium, citrate and malate are on a mole basis. The calcium citrate malate is referred to herein as CCM.

As used herein, the term "malic acid" refers to the mixture of the D and the L isomers, i.e. malic acid is optically active and the racemic mixture is used herein. D-malic acid and L-malic acid can be used.

As used herein the term "metastable" means that the material is not at equlibrium, and is a mixture of various crystalline and non-crystalline forms and solid solutions of the calcium ions, citrate ions and malate ions as well as salts of these materials. While the reaction kinetics would indicate that the calcium neutralizes all of the acid groups of citric and malic acid, or partially neutralizes depending on the ratio of the calcium to citric acid to malic acid, a molecular complex consisting of 2 moles of citrate and 3 moles of malate with 6 moles of calcium apparently does not form. But rather, an equilibrium is established between the salts and, when prepared by the process herein, a complex salt is formed. This complex salt is distinct from pure calcium citrate or pure calcium malate or simple mixtures thereof. The salt may be crystalline or micro crystalline, but may also represent an amorphous form or may contain solid solutions of calcium, citrate and malate ions.

This complex is thermodynamically an intermediate formed in the preparation of a dry form. Occasionally this reaction produces a product which is the most thermodynamically stable and is practically insoluble. The exact reason for this is not known.

The metastable materials probably have more than 1 crystalline state reflected by the presence of multiple hydration states. In addition, there are likely to be significantly different arrangements of the citrate and malate within the material. The physical and chemical data of these salts are consistent with the theory that there are non-crystalline regions within the powdered material which can hydrate to the point of behaving like a solution. It is important for the solubility characteristics of the calcium citrate malate that the apparent metastable structure be achieved.

Therefore, while the X-ray diffraction pattern indicates that there is some crystallinity, and that this material is different from calcium citrate or calcium malate, the exact structure of the material is not known.

The calcium citrate malate herein can exist in several states of hydration with from 2 to as many as 16 to 20 water molecules (e.g. a 6:2:3:8H$_2$O moiety exists).

A. Process for Making Metastable Calcium Citrate Malate

The calcium citrate malate is prepared by adding a calcium salt, as a powder or as an aqueous slurry, to an aqueous solution of citric acid and malic acid in the mole ratio necessary to make the desired calcium citrate malate material. When calcium carbonate is used, carbon dioxide evolves as the calcium carbonate is neutralized by the citric and malic acids. The reaction is stirred until the carbon dioxide stops evolving and it appears that the materials have reacted. It should be recognized that not all of the carbon dioxide will evolve; some will dissolve in the water. When calcium oxide is used, or another source of calcium is used, the material is stirred until the acids have been neutralized.

The malic acid can be in solution and the citric acid and calcium source added to it at the same time or separately. It is preferable to add the calcium source to the solution of citric and malic acids. In other words adding malic acid to a premix consisting of calcium and citrate ion mixture, is not acceptable since calcium citrate forms readily and precipitates. This prevents the formation of the metastable CCM salt.

Preferably, calcium carbonate is used as the calcium source. Other sources include calcium oxide and calcium hydroxide. Calcium chloride, calcium phosphate and calcium sulphate are not suitable for use herein since the anions make an acid solution, i.e. hydrochloric acid, sulfuric and phosphoric acid, respectively. They also affect the flavor of the calcium citrate malate.

A solid forms during the mixing of the calcium oxide or calcium hydroxide with the citric and malic acid. When these materials are used, it is necessary to mix the solution until all of the calcium appears to have dissolved. The calcium citrate malate complex will precipitate when its solubility is exceeded.

The preferred method of preparation is to prepare a highly concentrated aqueous solution of the calcium citrate malate which quickly and efficiently forces metastable calcium citrate malate out of solution. Concentrations of from 20% to 75% (weight of reactants) in water are preferred. More preferably the concentration is from 40% to 65%.

The reaction temperature can be ambient (20° C.) or higher. Preferably the temperature of the reaction is in the range of 30° C. to 80° C. Most preferably it is from 40° C. to 60° C.

This total mixture, which contains a supernatant CCM complex in solution as well as a solid can be dried. The solid can also be removed from the supernatant solution by filtration, centrifugation, or decantation and then the solid dried.

Drying can be done by forced air drying, convection drying, oven drying, freeze drying or spray drying. No matter what form of drying is used, the temperature of the drying should be less than 100° C. Above 100° C., the calcium citrate malate decomposes. When it decomposes, a less soluble mixture is made and the ratio of calcium to citric and malic acid is changed.

Preferably, when using forced air drying, the drying is accomplished on a thin layer of product at between 60° C. and 85° C. The product is layered to between 0.05 inches and 0.5 inches thick.

In spray drying, the solution and solid mixture is sprayed into a hot air column at 60° C. to 85° C. The pressure in the column is 600 to 900 millimeters of mercury.

Vibratory freeze drying, or other conventional freeze drying techniques can also be used. The mixture is placed on a tray at a thickness of from about 0.01 to about 1 inch and frozen. A vacuum of 0.01 to 1 millimeters of mercury is used and a temperature of less than 25° C. is maintained during the freeze drying operation.

The material is preferably dried until the amount of free or unbound water is less than 5%. Free water is water that is not a part of a CCM hydrate. The calcium citrate malate can form stable hydrate salts. The level of water, either as free water or as the hydrate is important for microbial stability and for handling. Too much water inhibits the ability to grind or tablet the material.

When forced air drying or freeze drying is used, the dried material is ground using any conventional grinding equipment and then sieved to a particle size of less than 1 millimeter. This particle size makes it easier to dissolve in foods and beverages and also represents a good particle size for tableting. Grinding and sieving should be done under anhydrous conditions or at low humidities to keep the metastable calcium citrate malate from rehydrating.

The ratio of calcium to citric acid to malic acid in the final product will depend upon the reactants used. Generally, the preparation of this material starting with pure calcium carbonate, citric acid and malic acid and drying the entire solution, including the supernatant liquid will produce a calcium citrate malate salt of the same ratio of the materials mixed. In making calcium citrate malate salts wherein the mole ratio of calcium are above 5, e.g. 6:2:3, 8:2:5 and 7:2:4, it is important to include the supernatent in the material to be dried since lower ratio salts could drop out of solution. The exact formula for the salts can be derived by measuring the percent of calcium, and the percentage of citric and malic acid in the solid material. It is important to remember that water also has to be analyzed since these materials readily form hydrate salts. The calcium level can be determined by atomic absorption measurements.

B. Description of the Product

The calcium citrate malate/metastable salt represents a soluble form of calcium, which is considerably more soluble than calcium citrate, calcium malate, or calcium carbonate. In addition, the calcium citrate malate prepared herein is considerably more soluble in dilute acid solutions.

The process herein can be used to make a variety of calcium citrate malate compositions. The mole ratio of calcium to citrate and malate determines the composition of the salts. The preferred salts for solubility and therefore for bioavailability are the neutral and acidic salts.

Neutral metastable calcium citrate malate compositions having the formula:

$$3x + 2y = 2z$$

wherein x is the moles of citrate, y is the moles of malate and z is the moles of calcium. When z is greater than these metastable compositions exhibit enhanced solubility and functionality. The 6:2:3 salt is more soluble than 5:2:2 and other neutral salts have shown even better solubility. The ratio derived from this expression is expressed as integers and the ratio is reduced to the lowest common denominator. For example, 12:4:6=6:2:3; 6:2:3 is not expressed as 3:1:1.5.

The enhanced solubility of these salts is unexpected since one would not expect the anions and the ratio of calcium to anions to play such a key role in solubility. Table I lists the preferred neutral salts and their solubility expressed as calcium in solution per weight of calcium citrate malate used. The exact method for determining this is described hereinafter.

TABLE I

| Calcium Citrate Malate | Class | % Ca w/w CCM Solubility |
| --- | --- | --- |
| 6:2:3 | Neutral | 91 |
| 5:1:1 | Basic | 45 |
| 5:2:2 | Neutral | 73 |
| 8:2:5 | Neutral | 89 |
| 4:2:3 | Acid | 100 |

The acidic salts, those wherein the levels of citric and malic acids is greater than the level of calcium $3x+2y>2z$ are also more soluble and therefore preferred compositions in terms of solubility and bioavailability.

The basic materials, i.e. those in which calcium is in excess ($3x+2y<2z$), are not preferred. These tend to be less soluble (see Table I) and also contain excess amounts of calcium starting material. The method of solubility used to determine the data in Table I is described in the Analytical Methods section below. Using this method, calcium carbonate has a solubility of 0 and calcium citrate is 13, whereas calcium malate is 66.

A 6:2:3 calcium citrate malate solid prepared by the process herein is more soluble in either 1% or 10% acetic acid at a concentration of 500 milligrams of calcium per 50 milliliters (ml) of water than calcium citrate or calcium malate.

The following table lists the solubility of calcium salts in water (25° C.):

| Calcium Salt | g Salt/100 ml $H_2O$ | Reference |
| --- | --- | --- |
| CCM 6:2:3 | 1.10 | |
| Calcium Malate.3 $H_2O$ | 0.4, (0.31) | 2, (1) |
| Calcium Citrate | 0.096 | 1 |
| Calcium Oxide | 0.1 | 1 |
| Calcium Hydroxide | 0.1 | 1 |
| Calcium Carbonate | 0.0056 (.0014) | 1 (2) |

CCM is metastable calcium citrate of this invention.
(1) "Solubilities", 4th Edition, by W. F. Linke
(2) CRC Handbook of Chemistry and Physics, 67th Edition, (American Chemical Society)

All ratios are on a mole basis, and all percentages are by weight basis unless otherwise specified. The following examples illustrate the preparation of the materials herein, and are exemplary and are not meant to limit the invention. The 6:2:3 is prepared as in Example I.

EXAMPLE I

| Materials | Amount (g) |
| --- | --- |
| Calcium Carbonate (99+% purity) | 300 |
| Citric Acid (Anhydrous, powder) | 192 |
| Malic Acid (DL, practical) | 201 |
| Distilled/Deionized Water | 1000 |

Procedure

To prepare about 500 grams of CCM (6:2:3) powder:

Dissolve 192 g of citric acid and 201 g of malic acid in 1000 ml of distilled-deionized water in a 2 liter glass beaker and stir with a teflon coated magnetic stir bar until solution is clear (about 5 minutes). Carefully add 300 g of $CaCO_3$ to the acids solution at ambient temperature. This solid is added quickly, but at a rate slow enough to control the carbon dioxide evolution and to avoid overflowing the beaker. The mixture is stirred for 3 hours at room temperature. After 3 hours, the mixture is transferred in total to a 12 inch by 16 inch stainless tray to yield a solution fill level of approximately 0.5–0.75 inch. The mixture is dried in an 80° C. forced air oven (model Blue-M Stabil-Therm) for 19 hours.

The tray is removed and allowed to cool to room temperature. The CCM solid is ground to pass through a #20 screen (84 microns particle size) with a Wiley mill.

The calcium citrate malate solid is stored in a cool, dry place to avoid increasing the level of hydration. The calcium level of the product is 20.73% corresponding to the octahydrate form.

EXAMPLE II

A metastable 6:2:3 calcium citrate malate is prepared as in Example I except that the material is freeze dried at a temperature of 25° C. and a vacuum 0.01 millimeters of mercury.

C. Analytical Methods

1. Solubility

Determine % Ca wt/wt in CCM (Calcium Citrate Malate) sample by analysis.

Calculate g CCM to achieve 0.1 g Ca in the sample.

Add 50 ml water at room temperature (about 20° C.) to the sample and stir 30 minutes.

The sample slurry is then filtered rapidly through Whatman #4 filter paper (3") lined Buchner funnel until all visible water is through, a slight vacuum is used. The filtrate is diluted to 100 ml with 5% HCl solution in water.

A 200 ul sample of this solution is diluted to 50 ml with 1 ml 5% lanthanum (as lanthanum oxide) and 5% HCl. The Ca is determined by atomic absorption. This is the soluble calcium.

The residue (on filter paper) is dissolved in 5% HCl and diluted to 200 ml. The calcium level is determined by atomic absorption as above. This is the insoluble Ca.

The total of soluble and insoluble Ca should equal 100 mg. The percent soluble calcium is easily calculated.

2. Ca Content of CCM

Dissolve 100 mg CCM in 5% HCl and dilute to 100 ml with 5% HCl. To 1 ml of this solution is added 1 ml 5% lanthanum (as lanthanum oxide) and the sample diluted to 100 ml with 5% HCl.

The Ca level is measured by atomic absorption using the following procedure:

Equipment

Perkin-Elmer Atomic Absorption Spectrophotometer Model 3030.

Stock Standard Solution

Calcium, 500 mg/L. To 1.249 g of primary standard calcium carbonate, $CaCO_3$, add 50 ml of deionized water. Add dropwise a minimum volume of 5% HCl (approximately 10 ml), to effect complete solution of the $CaCO_3$. Dilute to 1 liter with deionized water.

Light Sources

When using the calcium 239.9 nm line, the use of a multi-element (Ca-Mg) or (Ca-Mg-Al) hollow cathode lamp with a quartz window is recommended.

Flame Adjustment

The absorption of calcium is dependent on the fuel-/air ratio and the height of the light beam above the burner. Although maximum sensitivity is obtained with a reducing (fuel-rich) flame, an oxidizing (fuel-lean) flame is recommended for optimum precision.

Other Flames

Calcium determination appears to be free from chemical interferences in the nitrous oxide-acetylene flame. Ionization interferences should be controlled by the addition of alkali salt (0.1% or more potassium as chloride) to samples and standards. It is probably preferable to determine calcium in a nitrous oxideacetylene flame, especially in samples containing large amounts of silica.

Interferences

Slight ionization occurs in the air-acetylene flame, and can be controlled by the addition of an alkali salt (0.1% or more potassium as chloride) to samples and standards. Calcium sensitivity is reduced in the presence of elements which give rise to stable oxysalts. These elements include aluminum, beryllium, phosphorus, silicon, titanium, vanadium, and zirconium. This effect is reduced by the addition of 0.1–1.0% lanthanum or strontium.

Standard Atomic Absorption Conditions for Ca

| Wavelength (nm) | Slit (nm) | Sensitivity (mg/L) | Linear Range (mg/L) |
|---|---|---|---|
| 422.7 | 0.7 | 0.092 | 5.0 |
| 239.9 | 0.7 | 13.0 | 800.0 |

Recommended Flame: Air-acetylene, oxidizing (lean, blue).
Sensitivity with a flow spoiler and $N_2O-C_2H_2$ flame at 422.7 nm: 0.048 mg/L.

Standard Flame Emission Conditions for Ca

| Wavelength (nm) | Slit (nm) | Flame |
|---|---|---|
| 422.7 | 0.2 | Nitrous oxide-acetylene |

The calcium is determined by comparing the absorption with standard calcium solutions.

3. Determination of Citric and Malic Acids in Calcium Citrate Malate (CCM)

A CCM sample is dissolved in dilute HCl and the dissolved organic acids are determined by ion exclusion HPLC (high pressure liquid chromatography).

Reagents (99+ or certified grades)
Citric Acid, anhydrous
d,l Malic Acid
Tricalcium Dicitrate Tetrahydrate
Calcium Malate Trihydrate
0.2N HCl
1N $H_2SO_4$
Water

HPLC

| | |
|---|---|
| Pump | Kratos Spectroflow 400 |
| Injector | Waters WISP 710B |
| In-Line Filter | Rainin 0.5 u |
| Column and Precolumn | Bio Rad HPX-87H, 300 × 7.8 mm |
| Detector | Kratos Spectroflow 783 |
| Integrator | Hewlett Packard 3390A |

Procedure

A. Preparation of Stock Solutions

HPLC Mobile Phase-Pipet 1.5 mL of 1N $H_2SO_4$ into a 1 L volumetric flask. Dilute to volume with HPLC grade water and shake to mix. Filter through an 0.45 u filter and degas under vacuum.

B. Preparation of Standard

Weigh accurately 0.025 g each of citric and malic acid into a 25 ml volumetric flask. Add mobile phase and shake to dissolve acids. Dilute to volume with mobile phase and shake to mix thoroughly.

C. Sample Preparation

1. Weigh accurately 0.05 g of CCM powder or put liquid sample into a 10 ml volumetric flask. Dissolve in 0.2N HCl. Dilute to 10 ml with 0.2N HCl and shake to mix thoroughly. If the sample does not completely dissolve, add additional HCl until dissolution is complete or repeat with a smaller sample.

2. Transfer a few milliliters to an autosampler vial for injection.

D. Chromatographic Procedure

| | |
|---|---|
| Mobile Phase | Isocratic, 0.0015N $H_2SO_4$ |
| Flow Rate | 0.8 mL/min |
| Injection Volume | 25 μL |
| Detector | UV 210 nm, 0.1 absorbance units full scale |

Calculations

Weight % Acid = $(As/Astd) \times Cs \times 1000/SW$ where
As = peak area for acid in sample
Astd = peak area for acid in standard
Cs = concentration of acid in standard in mg/mL
for example if, for citric acid:
As = 3.26 E06
Astd = 1.72 E06
Cs = 1.02
SW = 51.4
then the weight % citric acid is (3.26 E06/1.72E06) × 1.02 × 1000/51.4 = 37.6%

4. Hydrate Level

Since CCM samples decompose when heated above 100° C. for extended periods, it is difficult to determine the water level by drying or dessication procedures. The water level of the sample is determined by subtracting the total calcium, citric and malic acid concentrations from 100. Any remaining material is water.

Most dissolved carbon dioxide from the preparation is lost during the drying so it is negligible. Any carbonate anions remaining in "basic CCMs" should be accounted for before calculating the water level.

What is claimed is:

1. A process for making a metastable calcium citrate malate comprising:
   a) adding a calcium source selected from the group consisting of calcium hydroxide, calcium carbonate, or calcium oxide to citric and malic acid and water, wherein the mole ratio of calcium is from 2 to 10, of citric is from 1 to 3, and of malic is from 1 to 5;
   b) mixing the solution until the citric and malic acids are neutralized by the calcium;
   c) drying the mixture at a temperature of less than 100° C.; and
   d) grinding the resultant solid product to a particle size less than 1 mm in size; and wherein the metastable calcium citrate malate has a solubility in water at about 20° C. of 75% or more weight % calcium per calcium citrate malate on 100 mg basis; and wherein the calcium citrate malate is represented by the formula $3x+2y=2z$ or $3x+2y>2z$, wherein x is the moles of citric, y is the moles of malic, and z is the moles of calcium.

2. A process according to claim 1 wherein the mole ratio of calcium is from 4 to 8 and the calcium citrate malate is neutral or acidic.

3. A process according to claim 2 wherein the calcium source is calcium carbonate.

4. A process according to claim 3 wherein the drying is freeze drying at a temperature of less than 25° C. at a pressure of from 0.01 to 1 mm Hg.

5. A process according to claim 4 wherein the mixture is spray dried at a temperature of less than 90° C. and a pressure of from 600 millimeter mercury to 900 millimeters of mercury.

6. A process according to claim 1 wherein the mixing is at a temperature of from 30° C. to 80° C.

7. A process according to claim 6 wherein the concentration of the calcium, citric and malic acids are from 20% to 75% in the water of step (a).

8. A process according to claim 7 wherein the concentration is from 40% to 65%.

9. A process according to claim 8 wherein the citric acid is added simultaneously with the calcium source to malic acid in water.

10. A metastable calcium citrate malate complex of the formula $3x+2y=2z$ wherein 3x, 2y and 2z are integers and wherein x is the moles of citrate, y is the moles of malate and z is the moles of calcium and wherein z is greater than 5; said complex having a solubility in water at about 20° C. of 75% or more weight percent calcium per calcium citrate malate on a 100 mg basis.

11. A complex according to claim 10 wherein $x=2$, $y=3$ and $z=6$.

12. A complex according to claim 10 wherein $x=1$, $y=2.5$ and $z=4$.

13. A complex according to claim 10 wherein $x=1$, $y=2$ and $z=3.5$.

14. A metastable calcium citrate malate complex of the formula $3x+2y>2z$ wherein $x=1$, $y=2$ and $z=3.5$.

15. A complex according to claim 14 wherein z is greater than 4.

16. A complex according to claim 14 wherein the solubility in water at about 20° C. is greater than 95%.

17. A complex according to claim 10 wherein the solubility in water at about 20° C. is greater than 85%.

18. A complex according to claim 10 wherein z is greater than 6.

* * * * *